United States Patent [19]
Kato et al.

[11] Patent Number: 5,245,403
[45] Date of Patent: Sep. 14, 1993

[54] APPARATUS FOR DETECTING EXTRANEOUS SUBSTANCES ON A GLASS PLATE

[75] Inventors: Noboru Kato, Hadano; Izuo Horai, Odawara; Toshihiro Kimura, Fujisawa; Mitsuyoshi Koizumi, Yokohama, all of Japan

[73] Assignee: Hitachi Electronics Engineering Co., Ltd., Tokyo, Japan

[21] Appl. No.: 813,837

[22] Filed: Dec. 27, 1991

[30] Foreign Application Priority Data

Dec. 27, 1990 [JP] Japan ................ 2-414979

[51] Int. Cl.$^5$ .............. G01N 21/00; G01J 4/00
[52] U.S. Cl. ............... 356/237; 356/239; 356/338; 356/369; 250/572; 250/563
[58] Field of Search ............... 356/364–369, 356/335–343, 237, 239, 445, 446; 250/225, 572, 578, 562, 563

[56] References Cited

U.S. PATENT DOCUMENTS

| | | | |
|---|---|---|---|
| Re. 33,991 | 7/1992 | Shiba et al. | 356/237 |
| 4,610,541 | 9/1986 | Tanimoto et al. | 356/237 |
| 4,614,427 | 9/1986 | Koizumi et al. | 356/237 |
| 4,669,875 | 6/1987 | Shiba et al. | 356/237 |
| 4,672,196 | 6/1987 | Canino . | |
| 4,893,932 | 1/1990 | Knollenberg | 356/338 |
| 4,914,309 | 4/1990 | Masaharu et al. . | |
| 4,999,510 | 3/1991 | Hayano et al. | 356/237 |

FOREIGN PATENT DOCUMENTS

| | | | |
|---|---|---|---|
| 75689 | 4/1983 | European Pat. Off. . | |
| 249031 | 12/1987 | European Pat. Off. . | |
| 3714305 | 11/1987 | Fed. Rep. of Germany . | |
| 60-38827 | 2/1985 | Japan . | |
| 0041038 | 2/1988 | Japan | 356/369 |
| 63-12249 | 3/1988 | Japan . | |
| 0259244 | 10/1989 | Japan | 356/237 |
| 0110355 | 4/1990 | Japan | 356/237 |
| 3-188491 | 8/1991 | Japan . | |
| 2119506 | 11/1983 | United Kingdom . | |

*Primary Examiner*—Richard A. Rosenberger
*Assistant Examiner*—Hoa Q. Pham
*Attorney, Agent, or Firm*—Fay, Sharpe, Beall, Fagan, Minnich & McKee

[57] ABSTRACT

An apparatus for detecting extraneous substances on a glass plate includes a first light projecting system arranged above a plane under examination on a glass plate, the surface of which is irradiated with an S-polarized laser beam at a first elevation angle, a second light projecting system arranged above the surface thereof which is irradiated with a P-polarized laser beam at a second elevation angle greater than the first elevation angle, and a light receiving system for receiving scattered light from the surface irradiated with the laser beams respectively emitted from the first and the second light projecting system at an elevation angle smaller than the first elevation angle. The light receiving system is arranged on a side opposite to the direction of irradiation with the normal line set up at the laser beam irradiation point therebetween and the output level of the P-polarized laser beam is set in specific relation to the S-polarized laser beam.

12 Claims, 7 Drawing Sheets

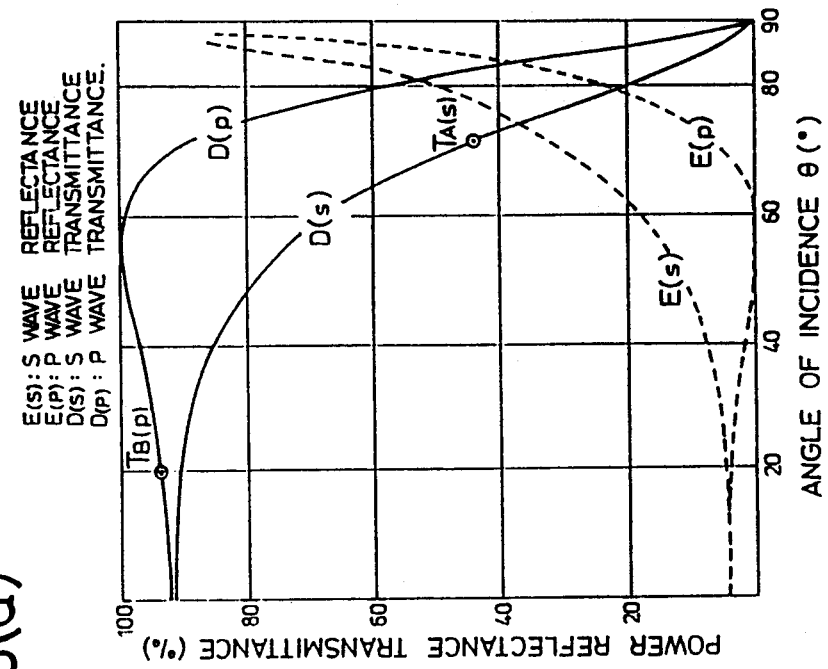
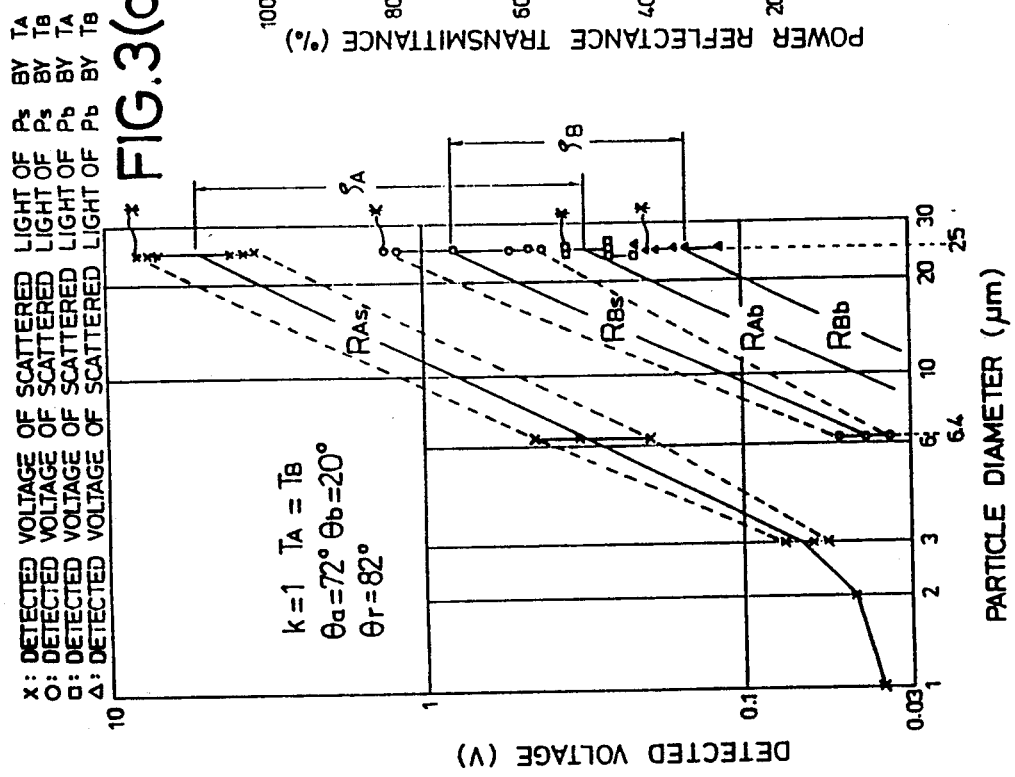
FIG.3(a)
FIG.3(b) PRIOR ART

APPARATUS FOR DETECTING EXTRANEOUS SUBSTANCES ON A GLASS PLATE

BACKGROUND OF THE INVENTION

1. Technical Field

The present invention relates generally to apparatus for detecting extraneous substances on an glass plates, and more particularly to an apparatus for detecting extraneous substances on a glass plate so that when extraneous substances are sticking to the front surface and the back surface of the glass plate, the extraneous substance sticking to the front surface thereof can be distinguished from what is sticking to the back surface before being detected.

2. Background Art

Flaw inspecting apparatus are generally used for detecting extraneous substances sticking to the surfaces of masking substrates (glass substrates) and silicon wafers for use in manufacturing semiconductor ICs, and to glass plates for use in liquid crystal panels and the like, the extraneous substances ordinarily including flaws such as defects of their surfaces themselves. Product quality is thus maintained at not lower than a certain level.

FIG. 5 shows a basic configuration of a flaw detecting optical system in an apparatus for detecting wafer surface flaws as a flaw inspecting apparatus of the sort described above by way of example. The optical system consists of a light projecting system 2 and a light receiving system 3. Laser beams emitted from a laser beam source 21 are focused by a light projecting lens 22. An optical spot is formed on the surface of a wafer plate 1 as an object under examination. When the optical spot scans the surface of the wafer plate 1 pursuant a revolving scanning or XY scanning method, it will be scattered at a place where a flaw is found. The scattered light is condensed by a condenser lens 31 in the light receiving system 3 and received by a light receiver 32. A flaw detection signal is thus obtained. A stopper 33 provided in the light receiving system 3 is inserted for improving the S/N ratio by cutting off the regular reflected light deriving from the laser beam.

With the basic configuration described above, various improvements have been introduced in light projecting and light receiving systems in not only optical systems for detecting wafer surface flaws but also those for detecting flaws on masking substrates, glass plates for use in liquid crystal panels and the like. For instance, it is commonly practiced to improve the condensation effect by means of optical fibers instead of the condenser lens 31 as a light receiving system.

A TFT-type liquid crystal panel is formed with an extra-fine liquid crystal pixel electrode and a thin-film transistor (TFT), formed by etching the surface of a glass plate. The surface of the glass plate (glass substrate) with the liquid crystal pixel electrode and TFT formed thereon is provisionally called a pixel formative plane, for instance. With extraneous substances sticking to the pixel formative plane, it is highly probable for a number of TFTs connected to each other to simultaneously malfunction. The extraneous substances sticking to that surface may seriously affect the quality of the liquid crystal panel as a product; this makes it necessary to use such a flaw detecting optical system for detecting the presence or absence of extraneous substances on the pixel formative plane of the glass substrate.

Incidentally, the glass substrate having a pixel formative plane is a plate which is translucent, as thin as about 1 mm and has high transmittance. Consequently, the problem is that extraneous substances sticking to the pixel formative plane (hereinafter simply called 'surface extraneous substance(s)') and those sticking to the back surface of the glass substrate (hereinafter simply called 'back surface extraneous substance(s)') may simultaneously be detected. The back surface of the glass substrate is normally used as a side where an image to be displayed is observed or where back light is transmitted therethrough when the glass substrate is assembled as part of a liquid crystal panel. This means the back surface of the glass substrate is only need to be a glass surface, and so long as extraneous substances sticking thereto are minute, they pose no problems; in other words, the extraneous substances are not regarded as flaws in many cases. In case these extraneous substances are detected as flaws, the otherwise good parts are assumed to be bad and the yield of parts tends to decrease, thus resulting in a heavy loss.

While the operation of detecting flaws on a glass substrate for a liquid crystal display panel is performed, only extraneous substances on a pixel formative plane on the surface side thereof as viewed from the liquid crystal are detected so that those on the back surface side may be ignored. However, the fact that the glass substrate is a thin plate having high transmittance makes it actually difficult to distinguish extraneous substances on the surface from those on the back surface.

The present inventors proposed the art of detecting extraneous substances on both sides separately, and the present applicants filed an application for a patent under the title "A Method of Detecting Surface Flaws on Liquid Crystal Panel", Japanese Patent Application No. 327966/1989, dated Dec. 18, 1989. Referring to FIGS. 6(a) and 6(b), a general description will subsequently be given of the method.

As shown in FIG. 6(a), a light projecting system 2 and receiving system 3 are provided above the pixel formative plane (hereinafter called the 'surface') of a glass substrate 1 as an object under examination, whereas a light projecting system 2 and receiving systems 3' are provided symmetrically about the glass substrate 1 on the back surface side thereof. Laser beams T, T' of substantially the same intensity are used respectively to form optical spots on the surface and the back surface, whereby alternate scanning is implemented. On the assumption that the sensitivities of the two light receiving systems 3, 3' are substantially identical, the detected signals of scattered light are compared. Of the detected signals in the light receiving system 3 on the surface side after the comparison is made, what is greater than the detected signal in the light receiving system 3' on the back surface side is defined as a flaw detecting signal concerning an extraneous substance, including a flaw, sticking to the surface.

A description will subsequently be given of the basic principle of making the above decision. FIG. 3(b) refers to cases where an extraneous substance Ps is sticking to the surface of the glass substrate 1 and where an extraneous substance Pb is sticking to the back surface thereof. In these cases, the light receiving system 3 on the surface side directly receives scattered light Rs deriving from the laser beam T at the surface extraneous substance Ps, and simultaneously irregular reflected light at the extraneous substance Pb on the back surface side. In other words, scattered light Rb at the extraneous substance Pb on the back surface side passes through the glass substrate 1 and reaches the light receiving system 3. Due to total reflection, the scattered light Rb attenuates as it passes through the glass substrate 1. As a result, the extraneous substance Ps on the surface side imparts to the light receiving system 3 scattered light that is more intense than what is directed to the light receiving system 3' on the back surface.

Such is also the case for an extraneous substance on the back surface side. The light receiving system 3' on the back surface side directly receives scattered light Rb' deriving from the laser beam T' at the extraneous substance Pb on the back surface side, and simultaneously irregular reflected light at the extraneous substance Ps on the surface side. In other words, scattered light Rs' at the surface extraneous substance Ps passes through the glass substrate 1 and reaches the light receiving system 3'. The scattered light Rs' also attenuates as it passes through the glass substrate 1. The extraneous substance Pb on the back surface side imparts to the light receiving system 3' scattered light more intense than what is directed to the light receiving system 3 on the surface side.

A comparison of the detected signals on both sides to find which one of the light receiving systems 3, 3', is receiving light that is more intense than the other makes it possible to determine whether the extraneous substance in question is located on the surface or the back surface side.

However, it has also frequently occurred that an extraneous substance on the surface side still remains inseparable from what exists on the back surface side when the above decision-making principle is actually applied and this has posed a problem. Since any apparatus using such a decision-making principle requires installing both light projecting and receiving systems on respective sides of an object under examination, the apparatus has proved unfavorable in view of its maintenance and the like as it tends to increase in size.

SUMMARY OF THE INVENTION

The present inventors have primarily given careful consideration to the prior art indistinguishability of respective extraneous substances on the surface and back surface sides when the above decision-making principle is actually applied, and have reasoned that the principle is based on a tacit understanding that the directivity of scattered light at the extraneous substance is uniform and omnidirectional. Referring to FIGS. 7(a), 7(b), a description will be given of this problem.

FIG. 7 shows the results of experiments made on the directivity of scattered light at an extraneous substance. As shown in FIG. 7(a), the intensity of scattered light R at an extraneous substance P in the direction of an angle $\epsilon$ from the direction of projection of a laser beam T is considered first. FIG. 7(b) shows experimental results by way of example. More specifically, FIG. 7(b) shows curves of the intensity F of scattered light at the angle $\epsilon(°)$ with the particle diameter as a parameter (1-10 $\mu$m). The intensity F of the scattered light drastically varies with the angle $\epsilon$. The intensity F of the scattered light is extremely great in the vicinity of an angle $\epsilon=0°$, that is, in the direction of projection (forward). When the particle diameter is 1 $\mu$m, for instance, the intensity is about 150 times greater in the direction of 90° (sideward). When the particle diameter is 10 $\mu$m, it is greater by about three digits in the direction of 90° (sideward). By this is meant that when the surface of a glass substrate is irradiated with the laser beam at an angle, the directivity is such that scattering at the angle $\epsilon=0°$, that is, forward scattering, is seen to be intense.

In consideration of the forward directivity, the decision-making principle is appraised on the assumption that a light receiving system 3 has an angle as shown in FIG. 6(a). Referring to FIG. 6(b), forward scattered light deriving from a laser beam T' and undergoing total reflection within a liquid crystal panel 1, rather than scattered light Rs deriving from the laser beam T at a surface extraneous substance Ps, may be received more intensely by the light receiving system 3. The forward scattered light deriving from the laser beam T, rather than scattered light Rb' deriving from the laser beam T' at an extraneous substance Pb on the back surface, may likewise be received more intensely by a light receiving system 3'. Therefore, it will be understood to be not always appropriate that a decision is made by simply comparing the sizes of the signals detected by both light receiving systems so as to separate the extraneous substances Ps, Pb. In FIG. 6(a), projection angles of respective light projecting systems 2, 2' and reception angles of the respective light receiving systems 3, 3' have not been specified.

In the present invention, special attention has been directed to the fact that there exist sturdy directivity in front of such scattered light, and consequently not only the optimum arrangement of light projecting and receiving systems but also optimum angles of projection and reception. The optimum configuration that has been contrived herein comprises the provision of such light projecting and receiving systems on one side where a pixel formative plane is formed accordingly, so that extraneous substances on the surface and the back surface are separately detected.

More specifically, an apparatus for detecting extraneous substances on a glass plate according to the present invention comprises a first light projecting system arranged above a plane (hereinafter called the 'surface') to be inspected of a glass plate, the surface of which is irradiated with an S-polarized laser beam at a first elevation angle. A second light projecting system is arranged above the surface thereof for irradiating the surface with a P-polarized laser beam at a second elevation angle greater than the first elevation angle, and a light receiving system is provided for receiving scattered light from the surface irradiated with the laser beams respectively emitted from the first and the second light projecting system at an elevation angle smaller than the first elevation angle. The light receiving system is arranged on a side opposite to the direction of irradiation with the normal line set up at the laser beam irradiation point therebetween, and the output level of the P-polarized laser beam is set in specific relation to the S-polarized laser beam. In this case, the presence of an extraneous substance on the surface is ultimately detected when a signal level obtainable in the light receiving system in response to the irradiation of the S-polarized laser beam is higher than a signal level obtainable in the light receiving system in response to the irradiation of the P-polarized laser beam.

The specific relation described above refers to a case where the output level of the P-polarized laser beam is set in such a way that a third and a fourth detection level are held between a first and a second detection level, wherein when an extraneous substance having a certain particle diameter on the surface is irradiated with the S-polarized laser beam, the level of the scattered light detected by the light receiving system is defined as the first detection level; wherein when the extraneous substance is irradiated with the S-polarized laser beam via the glass plate with its surface down, the level of the scattered light detected by the light receiving system is defined as the second detection level; wherein when the extraneous substance is irradiated with the P-polarized laser beam, the level of the scattered light detected by the light receiving system is defined as the third detection level; and wherein when the extraneous substance is irradiated with the P-polarized laser beam via the glass plate with its surface down, the level of the scattered light detected by the light receiving system is defined as the fourth detection level.

It is further needed to determine the presence of the extraneous substance, including a flaw, on the back surface only when the signal level obtainable in the light receiving system in response to the irradiation of the laser beam from the first light projecting system is lower than what is obtainable in the light receiving system in accordance with the irradiation of the laser beam from the second light projecting system.

In the case of an apparatus for detecting an extraneous substance, including a flaw, on the surface of a glass substrate for a liquid crystal panel, the first and second light projecting systems should preferably be provided above and opposite to the surface (pixel formative plane) of the glass substrate at the following angles: A light receiving system should be provided at a reception angle of about 10° perpendicular to the surface. Then the first light projecting system should be set at an elevation angle of about 20° as a projection angle and the second light projecting system at an elevation angle of about 7° as a projection angle. Moreover, the laser beam power of the second light projecting system is set in the range of 2-4 times the irradiation power of the laser beam of the first light projecting system.

Therefore, an object of the present invention is to provide an apparatus for detecting extraneous substances on a glass plate that has light projecting systems and a light receiving system on one side of the glass plate and is capable of detecting an extraneous substance on either the surface or the back surface of the glass plate separately from what is on the other.

Another object of the present invention is to provide an apparatus for detecting extraneous substances on a glass plate that has light projecting systems and a light receiving system on one side of the glass plate and is capable of detecting an extraneous substance on the surface of the glass plate separately from what is on the back surface thereof.

Still another object of the present invention is to provide an apparatus for detecting extraneous substances on a glass substrate that has light projecting systems and a light receiving system above a pixel formative plane and is capable of detecting an extraneous substance on the pixel formative plane side of the glass substrate for use in a liquid crystal panel separately from what is on the back surface side thereof.

A further object of the present invention is to provide an apparatus for detecting flaws of a glass plate that has light projecting systems and a light receiving system on one side of the glass plate and is capable of detecting a flaw on the surface side of the glass plate separately from what is on the back surface side thereof.

BRIEF DESCRIPTION OF THE DRAWINGS

FIGS. 3(a) and 3(b) show experimental data indicating different detection voltages of a photoelectric converter element with respect to an extraneous substance having the same particle diameter on the surface or the back surface in the optical system model of FIG. 2, and curves exhibiting the reflection factor and transmittance of a glass substrate.

DESCRIPTION OF THE PREFERRED EMBODIMENT

Figure 1:
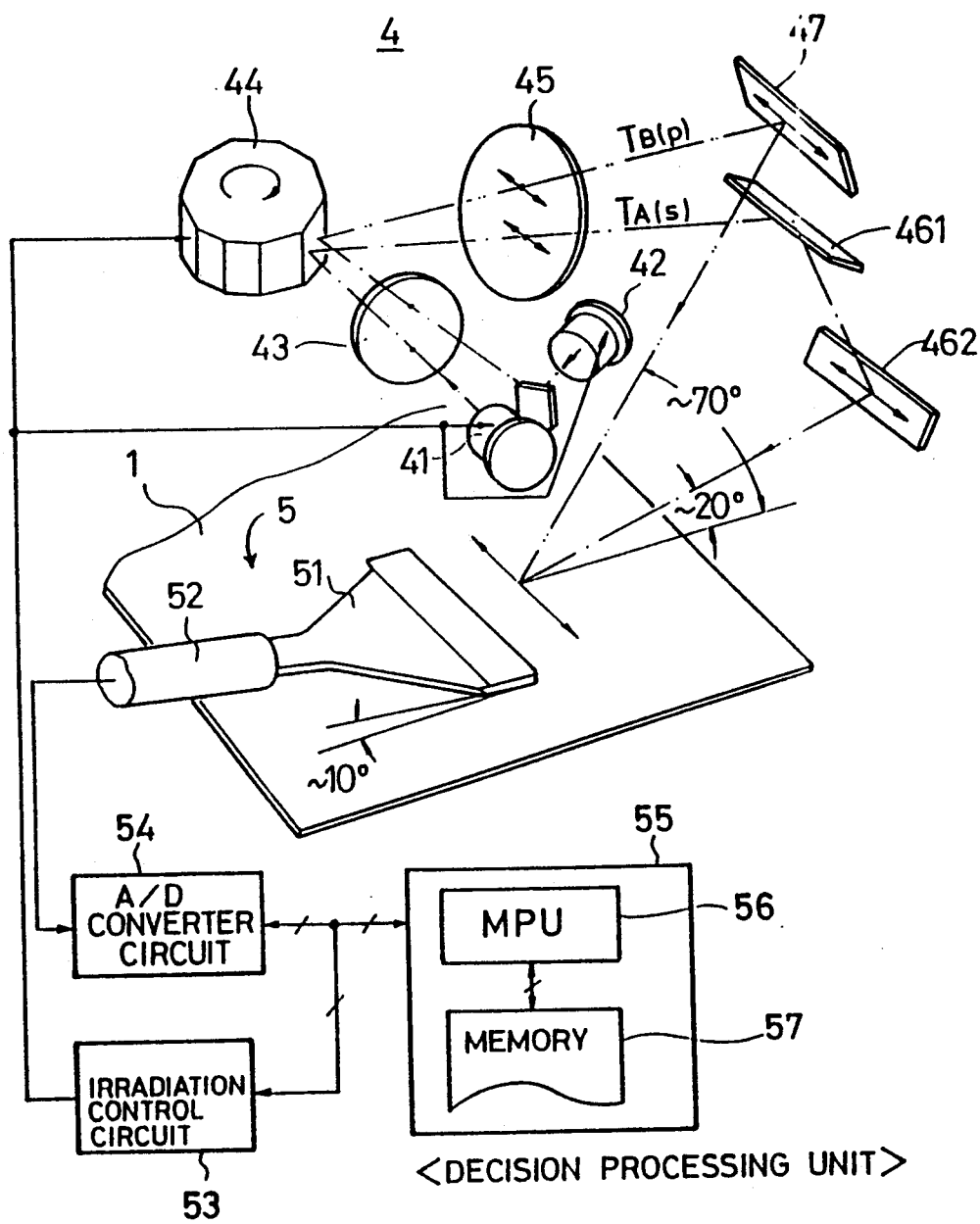
FIG. 1 is a diagram illustrating a configuration of an apparatus for detecting extraneous substances on the surface of a glass plate according to the present invention.

As shown in FIG. 1, an apparatus 10 for detecting surface extraneous substances on a glass plate has a laser source 41 for generating an S-polarized laser beam $T_A(s)$ and a laser source 42 for generating a P-polarized laser beam $T_B(p)$ by means of a semiconductor laser element, both the sources being located above a glass substrate 1, as an object under examination, such as a liquid crystal panel. An irradiation control circuit 53 drives the laser sources 41, 42 alternately and causes them to generate the S-polarized laser beam $T_A(s)$ and P-polarized laser beam $T_B(p)$ alternately. The irradiation control circuit 53 is controlled by a decision processing unit 55, which also interlockingly controls the driving of the laser sources and the rotation of a rotary mirror 44. In this case, the P-polarized laser beam $T_B(p)$ has power k times (2-4 times) greater than that of the laser beam $T_A(s)$. The mirror 47 is irradiated with each of the laser beams $T_A(s)$, $T_B(p)$ via a collimator lens 43, a rotary mirror 44 and a lens 45, and each laser beam is subjected to collimation, angle sweep and focusing commonly and successively via these optical systems. As a result, an optical spot is formed on the surface (pixel formative plane) of the glass plate 1 and used for surface scanning.

The laser beam $T_A(s)$ thus focused is changed in direction by two of the mirrors 461, 462 and projected onto the surface of the glass substrate at a projection angle (elevation angle) of about 20°. The laser beam $T_B(p)$ is changed in direction by the mirror 47 and projected at a projection angle (elevation angle) of about 70° for scanning the same straight line that is scanned by the laser beam $T_A(s)$ on the glass substrate 1. The irradiation control circuit 53 synchronously controls the period of the alternate driving of the laser sources 41, 42 and the rotating speed of the rotary mirror 44 for scanning purposes.

Scattered light obtainable at an extraneous substance at the time of laser beam irradiation is received by a light receiving system 5 situated at a reception angle (elevation angle) of about 10° with respect to the surface of the glass substrate 1. The scattered light is condensed by a bundle 51 of optical fibers and the light thus condensed is supplied to a photoelectric converter element 52 in which it is converted into an electric signal. Detected voltage corresponding to the quantity of light received is produced from the photoelectric converter element 52. The detected voltage is divided into detected voltages $R_A$, $R_B$ in accordance with the timing at which the driving of the laser source is controlled by the irradiation control circuit 53, and these voltages are sampled by an A/D converter circuit 54. The sampling timing in the A/D converter circuit 54 is controlled by the decision processing unit 55 as well as the irradiation control circuit 53.

Each of the detected voltage values resulting from the conversion implemented in the A/D converter circuit 54 correspondingly after laser beam irradiation is read by a microprocessor (MPU) 56 and stored in a memory 57 in the decision processing unit 55. The storage operation is performed together with the relevant scanning position (position coordinates on the X- and Y-planes of the glass substrate 1) on the glass substrate 1. The decision processing unit 55 subsequently executes a predetermined decision processing program to obtain the difference between the detected voltages and decides whether they are equal or which of them is greater. The decision processing unit 55 further decides the presence of a surface extraneous substance when both voltages are equal or when one of them is greater. In this case, data intended for use in computing the difference between the voltage values are concerned with what is higher than noise level.

In this embodiment, the reception angle of the light receiving system 5 is set at about 10°, which is smaller than an angle at which regular reflected light is received from either the first or the second light projecting system. When neither the surface nor the back surface has an extraneous substance, the light receiving system receives 5 almost no scattered light. However, as the light receiving system 5 may still receive some scattered or disturbed light from the back surface even when no extraneous substances exist on either side, the detected voltage values resulting from the reception of light are processed to identify them as noise levels, and only those representing that extraneous substances are actually detected are taken up for the intended purpose.

When the outputs of the laser beams $T_A(s)$, $T_B(p)$ are assumed equal, with the detection optical system configuration above, the following relation is established.

While the laser beam $T_A(s)$ is projected onto the surface of the glass substrate at a projection angle of about 20° in the embodiment shown, the light receiving system for receiving the scattered light is arranged at a reception angle of about 10° in the forward direction of light reception. The quantity of scattered light incident on the light receiving system 5 out of the scattered light in front of the surface extraneous substance due to the laser beam $T_A(s)$ is consequently large. On the other hand, scattered light in front of the back surface extraneous substance due to the laser beam $T_A(s)$ considerably attenuates because of internal reflection within the glass substrate. Moreover, since the quantity of transmitting light is generally smaller than that of reflected light in the S-polarized laser beam, scattered light originating from the back surface extraneous substance and entering the light receiving system located on the surface side is small in quantity and therefore the difference between the detected voltages tends to increase.

With respect to the light projecting system 4, the laser beam $T_B(p)$ is projected at a projection angle of about 70° from the surface of the glass substrate 1 (20° as viewed from the normal line), whereas the light receiving system 5 for receiving the scattered light is situated at an angle of about 10° from the surface (about 80° as viewed from the normal line), whereby the light receiving system receives light sidewise at an angle of about 100°. Consequently, the scattered light incident on the light receiving system 5 out of the scattered light at the surface and the back surface extraneous substance becomes less intense than that derived from the laser beam $T_A(s)$. FIG. 3(a) is a graph illustrating such a state as will be described later.

The voltage detected in the light receiving system 5 with the irradiation of the laser beam $T_A(s)$ is represented by $R_A$, and the voltage detected therein with the irradiation of the laser beam $T_B(p)$, by $R_B$. With the irradiation of the laser beam $T_A(s)$, further, the voltage detected when a surface extraneous substance is detected is represented by $R_{As}$ (the accompanying s means the surface extraneous substance) and the voltage detected when a back surface extraneous substance is detected, by $R_{Ab}$ (the accompanying b means the back surface extraneous substance). With the irradiation of the laser beam $T_B(p)$ likewise, the voltage detected when a surface extraneous substance is detected is represented by $R_{Bs}$ and the voltage detected when a back surface extraneous substance is detected, by $R_{Bb}$. Assuming the light irradiation power of the laser beam $T_A(s)$ and the laser beam $T_B(p)$ directed to the surface of the glass substrate 1 is equal, the following relation is established among the detected voltages when the order of their intensity is considered:

$$R_{As} > R_{Bs} > R_{Ab} > R_{Bb} \tag{1}$$

$$R_{As} - R_{Bs} > R_{Ab} - R_{Bb} \tag{2}$$

However, these are related to each other in substantially the same way even if $R_{As}/R_{Ab}$ and $R_{Bs}/R_{Bb}$ ratios are chosen for use.

FIG. 3 shows it is obtainable from measurement that the detected voltages remain in the above size relation.

Figure 2:
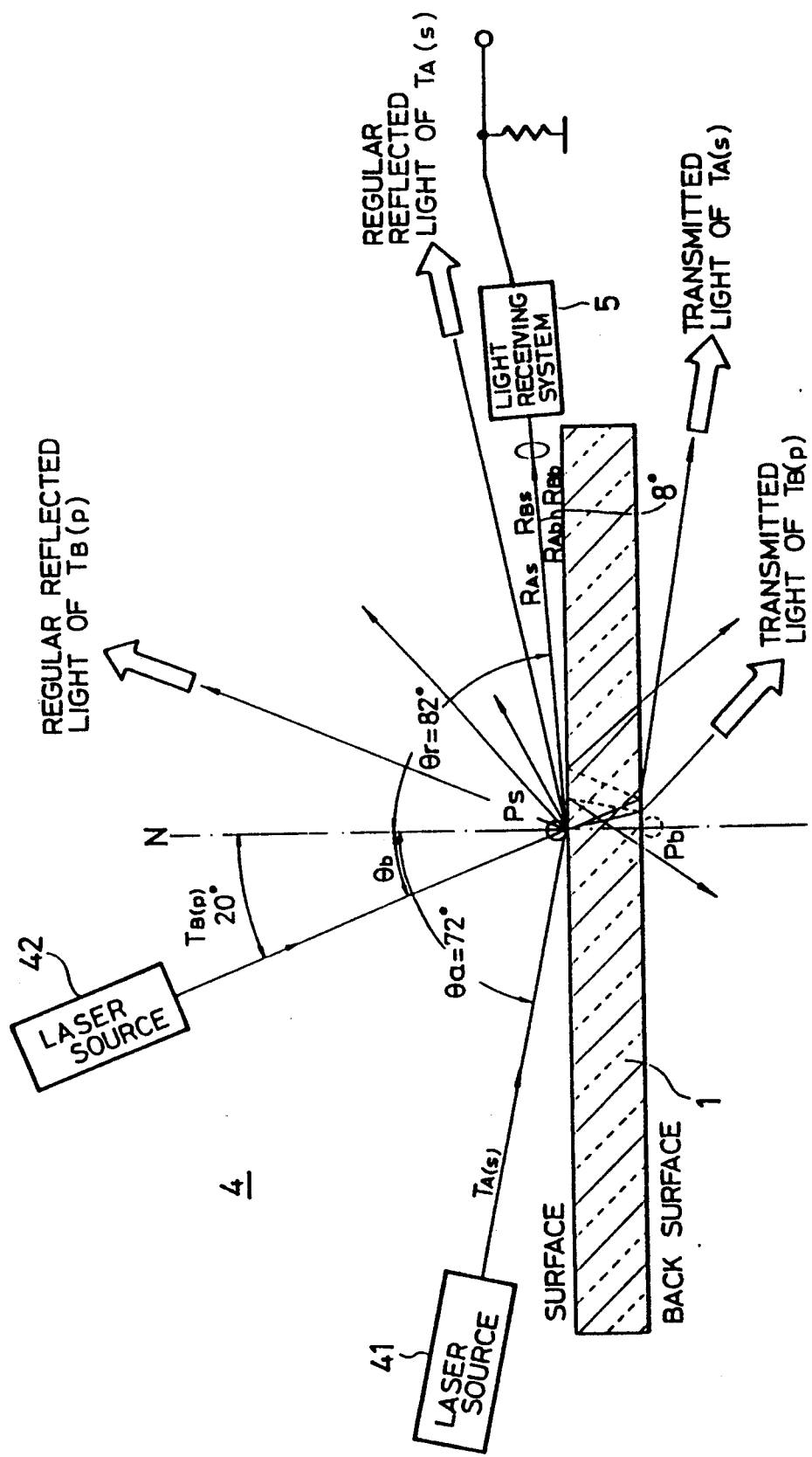
FIG. 2 is a diagram illustrating a model optical detecting system constructed according to the teachings of the present invention.

In FIG. 2, Ps indicates standard particles of various particle diameters sticking to the surface of the glass substrate 1. A plurality of standard particles sticking to the surface are made to constitute the surface extraneous substance Ps and then the glass substrate 1 is turned upside down to make the surface extraneous substance a back surface extraneous substance. With this arrangement, the surface and the back surface may be examined in such a state that an extraneous substance of the same variety is sticking to both sides. The S-polarized laser beam $T_A(s)$ is projected from the laser source 41 provided above the glass substrate at a projection angle of 18° (incident angle $\Theta a = 72°$) Moreover, the P-polarized laser beam $T_B(p)$ is projected from the laser source 42 at a projection angle of 70° (incident angle $\Theta b = 20°$) In this case, the outputs of the laser beam $T_A(s)$ and the laser beam $T_B(p)$ are adjusted to be equal. Further, the semiconductor laser elements of the laser sources 41, 42 are driven alternately to oscillate under the control of the light irradiation control circuit 53.

As an example of the case with an angle of 10°, the light receiving system 5 is provided in the direction of 8° (reflection angle $\Theta r = 82°$) from the surface of the glass substrate. The detected voltages ($R_{As}$, $R_{Ab}$), ($R_{Bs}$, $R_{Bb}$) of scattered light at the extraneous substance on the surface or the back surface in response to the irradiation of the laser beams $T_A(s)$, $T_B(p)$ are obtained alternately from the light receiving system 5. As the detected voltages at that time, data shown in FIG. 3(a) were obtained. In this case, $\rho_A$, $\rho_B$ represent detected voltages corresponding to the logarithmic difference between irregular reflection from the surface and reflection from the back surface in response to the irradiation of the laser beams $T_A(s)$, $T_B(p)$, respectively. In other words, $\rho_A$ designates the mean value of the logarithmic difference between the detected voltages $R_{As}$, $R_{Ab}$ with the irradiation of the laser beam $T_A(s)$, whereas $\rho_B$ designates the mean value of the logarithmic difference between the detected voltages $R_{Bs}$, $R_{Bb}$ with the irradiation of the laser beam $T_B(p)$. As illustrated, $\rho_A$ indicates a difference of one digit or greater between the detected voltages, whereas $\rho_B$ indicates a difference of less than one digit therebetween.

Since the surface extraneous substance Ps with the irradiation of the laser beam $T_A(s)$ causes intense forward scattered light as shown in FIG. 3(a), the detected voltage $R_{As}$ (marked with X) shows a maximum value at any point as shown in data on each of the particle diameters (3 μm, 6.4 μm and 25 μm). Although the back surface extraneous substance Pb also causes intense forward scattered light, it conforms to the value ($1/\rho_A$ as illustrated) of the detected voltage $R_{Ab}$ (marked with □) as it considerably attenuates because of internal reflection within the glass substrate. In the case of the laser beam $T_B(p)$, on the other hand, it is received sidewise as the light receiving system is situated at an angle of 102° ($=\Theta b + \Theta r$) from the incidence path For this reason, directivity relating to the intensity of scattered light stays in a weak region and this results in the detected voltage $R_{Bs}$ (marked with ○) lower than the detected voltage $R_{As}$ (marked with X). Moreover, the detected voltage $R_{Bb}$ (marked with Δ) becomes lower by $1/\rho_B$ than the detected voltage $R_{Bs}$ (marked with ○) because of internal reflection within the glass substrate 1. The plurality of particles are tested and the results marked with symbol * (25 μm) designate detected voltages relating to one and the same particle. As the detected voltages relating to the other particles are substantially arranged in order, the data are considered sufficiently reliable. Then the mean value of those detected voltages is obtained and straight lines of the detected voltages $R_{As}$, $R_{Bs}$, $R_{Ab}$ and $R_{Bb}$ are regarded as those indicating representative values.

If the transmittance of the glass substrate 1 and the influence of the internal reflection are then identical with respect to the laser beams $T_A(s)$, $T_B(p)$, the straight line ratios $R_{As}/R_{Ab}=\rho_A$ and $R_{Bs}/R_{Bb}=\rho_B$ should be identical. However, the actual values $\rho_A \approx 17$, $\rho_B \approx 6$ differ from each other. The main reason for this is that the laser beams $T_A(s)$, $T_B(p)$ are S-polarized and a P-polarized light waves, respectively.

FIG. 3(b) shows transmittance curves of polarized light waves with respect to a glass substrate for use in a generally known liquid crystal panel. First, the S-polarized light wave incident at an incident angle $\Theta(°)$ is reflected from the surface of the glass substrate and the reflection factor of power is indicated with a dotted line of E(s). On the other hand, the reflection factor of power of the P-polarized light wave is indicated with E(p). No reflection occurs in the vicinity of the Brewster's angle (57° when n=1.5) determined by the refractive index n of the glass substrate. Consequently, the characteristics of both curves differ from each other. In view of this, the reflection factor of the S-polarized laser beam is greater than that of the P-polarized one with the incident angle ranging from about 20° to about 85° in the case of the glass substrate for use in a liquid crystal panel.

In consideration of the fact that transmitted light in the glass substrate is reflected twice from the surface and the back surface, on the other hand, power transmittance curves D(s), D(p) are obtained from the S-polarized and the P-polarized light wave. When the laser beams $T_A(s)$, $T_B(p)$ are applied to these curves, the transmittance of the P-polarized laser beam is greater than that of the S-polarized laser beam with the incident angle ranging from about 20° to about 85°. The transmittance of the laser beam $T_A(s)$ in the preceding example of $\Theta a = 72°$ is about 44%, whereas the transmittance of the laser beam $T_B(p)$ in the preceding example of $\Theta b = 20°$ is about 94%. This explains why $\rho_B$ is smaller than $\rho_A$. However, $\rho_A$ and $\rho_B$ will not become identical even though the transmittance is corrected. This is because the condition of the internal reflection is variable, depending on the direction of polarization of the light wave.

Figure 4A:
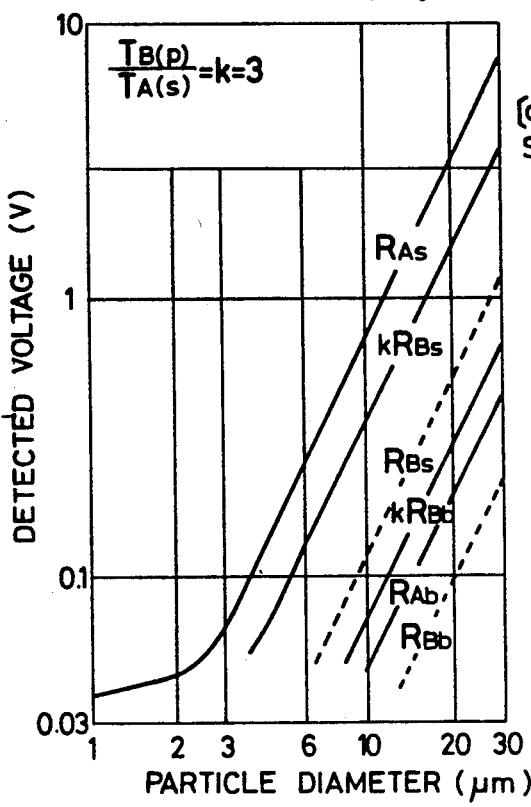
FIGS. 4(a), 4(b) and 4(c) are diagrams illustrating decision-making conditions for use in detecting the presence of surface and back surface extraneous substances and a preferable range of angles to be set for light projecting and receiving systems according to the present invention.

Now assuming the power of laser beam $T_B(p)$ is set to be k (=3) times greater than that of the laser beam $T_A(s)$ as shown in FIG. 1, the straight lines $R_{Bs}$, $R_{Bb}$ of FIG. 3(a) are increased by k times and moved from a dotted line position to an actual line one as shown in FIG. 4(a). The order of intensity of the respective straight lines then satisfies the following relation:

$$R_{As} > kR_{Bs} > kR_{Bb} > R_{Ab} \tag{3}$$

$R_{As} > kR_{Bs}$ is derived from the above equation as the condition of deciding the presence of the surface extraneous substance and $R_{Ab} < kR_{Bb}$ as the condition of deciding the presence of the back surface extraneous substance. Therefore, the presence of either one may be decided by comparing the detected voltages $R_A$, $R_B$ in amplitude. Although it is inconceivable to decide the presence of either one when $R_A = R_B$, the safety precaution is to side with the surface extraneous substance.

In this way, the decision processing unit 55 decides the presence of the surface extraneous substance when $R_A - R_B$ is positive in value or when $R_A/R_b$ is not less than 1; it is acceptable to presume the presence of the back surface extraneous substance from the result in reverse.

In this apparatus 10 for detecting a surface extraneous substance on a glass substrate, the output of the laser beam $T_B(p)$ may be switched selectively in such a way that it becomes k (2-4) times greater in intensity than that of laser beam $T_A(s)$. The detected voltages $R_{Bs}$, $R_{Bb}$ deriving from the laser beam $T_B(p)$ are then equally set to be k times greater. The multiple k is very important in the sense that the order of the detected voltage in size is varied as shown in FIG. 4(a).

The overall operation of the apparatus for detecting a surface extraneous substance on a glass substrate as shown in FIG. 1 comprises the following steps. The decision processing unit 55 causes the surface of the glass substrate 1 to be irradiated with the laser beam $T_A(s)$ and the laser beam $T_B(p)$ having an output k times greater so as to scan the surface of the glass substrate 1 to collect voltage R with respect to scattered light in response to the scanning position, so that the respective results are stored in the memory 57. Subsequently, MPU 56 obtains the difference between the detected voltages $R_A$, $R_B$ with respect to the same scanning position. In consideration of the order of the size above, the extraneous substance detected when $R_A \geq R_B$ is determined to be sticking to the surface (pixel formative plane side) of the glass substrate, and when $R_A < R_B$, the extraneous substance is designated as a back surface extraneous substance. However, as it is inconceivable to decide the presence of either one when $R_A = R_B$, the safety precaution is to side with the surface extraneous substance.

The process of deciding the presence of such a surface or back surface extraneous substance by means of the decision processing unit 55 may comprise the steps of collecting data on either of the detected voltages $R_A$ or $R_B$ corresponding to respective measurement coordinates on the glass substrate 1 beforehand, storing the resulting data in the memory 57, storing the detected data on the opposite side in the memory 57, and reading the detected data on the detected voltages $R_A$ or $R_B$ that have been collected correspondingly.

Figure 4B:
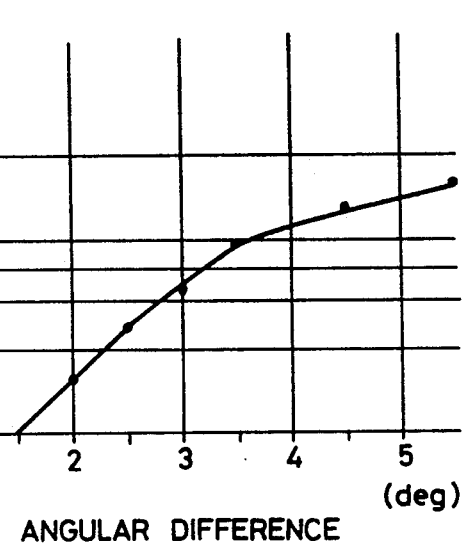

As set forth above, the angles at which two of the light projecting and receiving systems are installed only need to basically satisfy Eq. (3) in detection of extraneous substances or flaws. In consideration of not only noise but also scattered light from the back surface side of the glass, it would be necessary to examine the angles of the light projecting and receiving systems for the laser beam $T_A(s)$ as ranges for eliminating noise resulting from the reception of scattered light and the like from the back surface side and obtaining detected voltages effective in making a decision. With a glass substrate for use in a liquid crystal panel roughly ranging from one to several millimeters in thickness, its angle is set in an elevation angle range smaller by about 2° than that of the elevation angle of the light projecting system of the laser beam $T_A(s)$ in order for the regular reflected light from the light projecting system of the laser beam $T_A(s)$ to be unreceivable. At the angle of the light receiving system as an output level free from noise, the detected voltage whose level exceeds the noise level is generated even though there is no extraneous substance, as shown in the S/N ratio shown in FIG. 4(b), when the difference between the elevation angle of the light receiving system and those of projecting systems decreases to 2° or less.

Figure 4C:
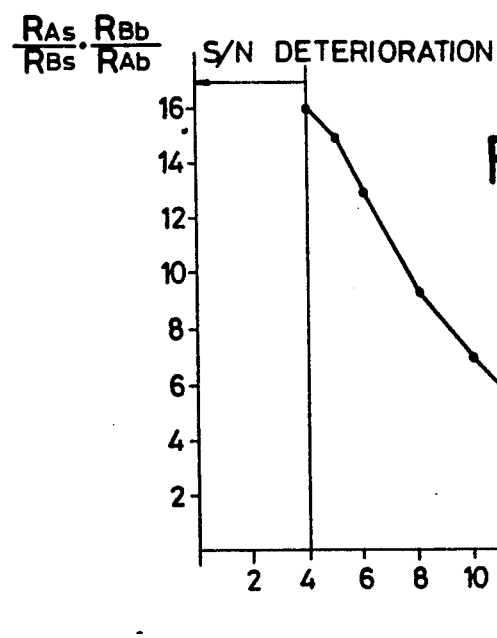
Figure 5:
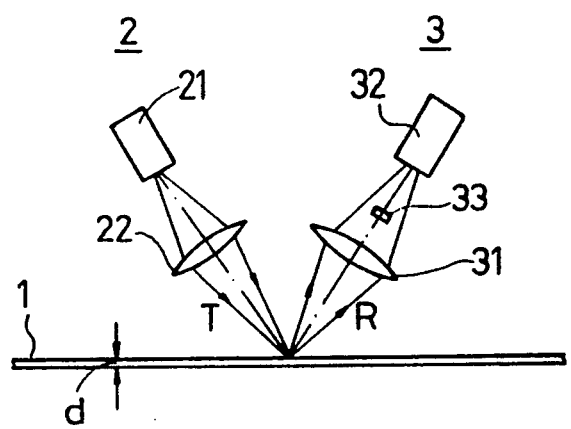
FIG. 5 is a diagram illustrating a basic configuration of an optical system in a conventional apparatus for detecting wafer surface flaws.
Figure 6A:
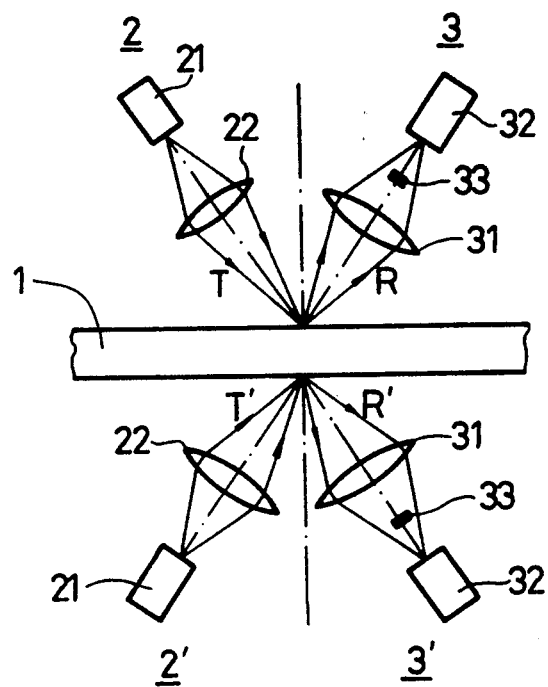
FIGS. 6(a) and 6(b) are diagrams illustrating a schematic configuration of the principle of separately detecting extraneous substances on both sides.
Figure 6B:
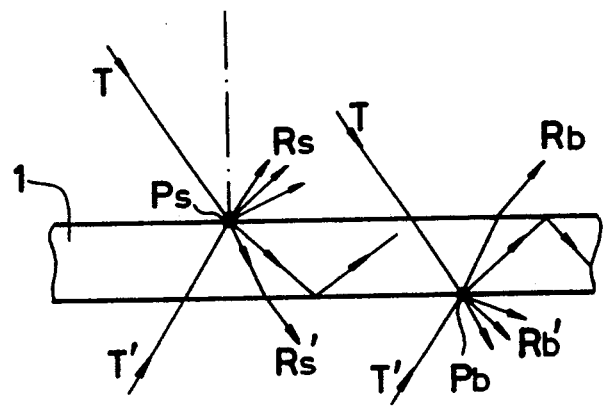

Moreover, the extraneous substance detection level on the back surface side is lower than that on the surface side. Consequently, the back surface extraneous substance S/N ratio that has been taken reveals the fact that, as shown in FIG. 4(c) illustrating the S/N ratio in the characteristics of $(R_{As}/R_{Bs}) \times (R_{Bb}/R_{Ab})$, the irregular reflection from the back surface of the glass substrate exceeds the noise level and is received if the light receiving system is situated at an angle of 5° or greater even when there exists no back surface extraneous substance. If the light receiving system is situated at an angle exceeding 16°, the detected output on the back surface side becomes excessive when any extraneous substance exists on the back surface and a value of $(R_{As}/R_{Bs}) \times (R_{Bb}/R_{Ab})$ decreases to 1.5 or less, thus making it difficult to separate both sides from each other. The elevation angle of the light receiving system should preferably substantially range from 5° to 15°. As a result, it is preferred for the light projecting system of the laser beam $T_A(s)$ to be angled at 7° or larger.

Figure 7A:
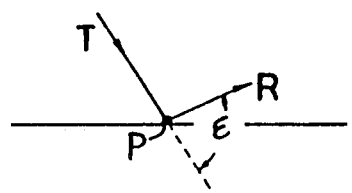
FIGS. 7(a) and 7(b) are diagrams illustrating the directivity of scattered light at an extraneous substance in the direction of projection of a laser beam.
Figure 7B:
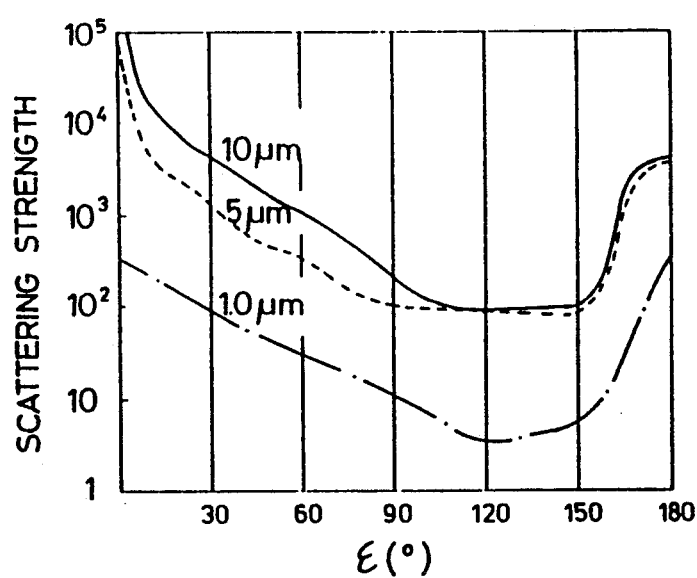

As shown in FIG. 7(b), an effective light detecting angle ranges up to about $\angle \epsilon = 100°$ in the forward direction of the light projecting system. Therefore, the maximum incident angle of the light projecting system responsive to the laser beam $T_A(s)$ becomes 25° and its elevation angle is set at 75°. Like the embodiment shown, moreover, the difference in elevation angle between the light projecting systems relating to the respective laser beams $T_A(s)$, $T_B(p)$ should be not less than 50° to make the difference between the detected voltages $R_A$ and $R_B$ about one digit or greater in responsive to the irradiation of the laser beam $T_A(s)$. Therefore, the angle of the light projecting system relating to the laser beam $T_A(s)$ should be set at not more than 25°. In other words, the angle of light projecting system relating to the laser beam $T_A(s)$ should preferably range from 7° to 25°, whereas what relates to the laser beam $T_B(p)$ should preferably range from 57° to 75°.

In the case of a glass substrate for use in a liquid crystal panel about 1 mm thick, the more preferable range empirically considered is such that the light receiving system should be provided at an elevation angle of about 10°±3°. Any extraneous substance may be detected in such a preferable state as what is understood in reference to the angle setting shown in the embodiment above, wherein with respect to the projection angle of the laser beam $T_A(s)$, it is set at an elevation angle of about 20°±3° and with respect to that of the laser beam $T_B(p)$, it is set at an elevation angle of about 70°±3°.

What is claimed is:

1. An apparatus for detecting an extraneous substance on a glass plate, the apparatus comprising a first light projecting system for irradiating the surface of the glass plate with an S-polarized laser beam at a first elevation angle as viewed from the surface thereof under examination for extraneous substance detection, a second light projecting system for irradiating the surface under examination with a P-polarized laser beam at a second elevation angle greater than the first elevation angle, and a light receiving system for receiving scattered light from the surface under examination, which has received laser beams from the first and the second light projecting systems, at a third elevation angle smaller than the first elevation angle, and the light receiving system being arranged so that the normal line to the surface at the laser beam irradiation point is located between the first and second light projecting systems and the light receiving system, wherein a first detection level is defined as a detection level of the scattered light detected in the light receiving system when an extraneous substance having a particle diameter on the surface under examination is irradiated with an S-polarized laser beam, a second detection level is defined as a detection level of the scattered light detected in the light receiving system when the extraneous substance is irradiated, via the glass substrate, with the S-polarized laser beam, with the glass plate being turned upside down, a third detection level is defined as a detection level of the scattered light detected in the light receiving system when the extraneous substance is irradiated with the P-polarized laser beam, and a fourth detection level is defined as a detection level of the scattered light detected in the light receiving system when the extraneous substance is irradiated with the P-polarized laser beam via the glass plate with the glass plate turned upside down; wherein the output level of the P-polarized laser beam is set so that the third and fourth detection levels fall between the first and second detection levels; and wherein when the signal level obtainable by the light receiving system which corresponds to the irradiation of the S-polarized laser beam is greater than the signal level that is obtainable thereby correspondingly to that of the P-polarized laser beam, the extraneous substance is judged to exist on the surface under examination.

2. An apparatus for detecting an extraneous substance on a glass plate as claimed in claim 1, wherein the output of the second laser beam from the second light projecting system ranges from two to four times greater than that of the first light projecting system.

3. An apparatus for detecting an extraneous substance on a glass plate as claimed in claim 2, wherein the extraneous substance is a flaw of the glass plate.

4. An apparatus for detecting an extraneous substance on a glass plate as claimed in claim 1, wherein the glass plate is a glass substrate for use in a liquid crystal panel and wherein its first elevation angle ranges from 7° to 25°, second elevation angle from 57° to 75°, and third elevation angle from 5° to 15°.

5. An apparatus for detecting an extraneous substance on a glass plate as claimed in claim 1, wherein the output of the laser beam in the second light projecting system is within the range of two to four times greater than the output of the laser beam in the first light projecting system, and wherein the glass plate is a glass substrate for use in a liquid crystal panel, with a first elevation angle toward the surface under examination ranging from 7° to 25°, a second elevation angle ranging from 57° to 75°, and a third elevation angle ranging from 5° to 15°.

6. An apparatus for detecting an extraneous substance on a glass plate as claimed in claim 5, wherein the difference between the first and the second elevation angle is either equal to or greater than 50°.

7. An apparatus for detecting an extraneous substance on a glass plate as claimed in claim 6, wherein the first elevation angle ranges from 17° to 23°, the second elevation angle from 67° to 73°, and the third from 7° to 13°.

8. An apparatus for detecting an extraneous substance on a glass plate as claimed in claim 7, wherein said glass substrate is about 1 mm thick and is formed as an electrode for liquid crystal display on the surface under examination.

9. An apparatus for detecting an extraneous substance on a glass plate as claimed in claim 8, wherein the first elevation angle is about 18°, the second about 70° and the third about 8°.

10. An apparatus for detecting an extraneous substance on a glass plate as claimed in claim 1, wherein when the signal level which corresponds to the irradiation of the P-polarized laser beam and is obtainable from the light receiving system is greater than what corresponds to the irradiation of the S-polarized laser beam and is obtainable therefrom, the resulting extraneous substance is decided as an extraneous substance existing on the back surface under examination.

11. An apparatus for detecting an extraneous substance on a glass plate as claimed in claim 1, wherein when the signal level which corresponds to the irradiation of the S-polarized laser beam and is obtainable from the light receiving system is greater than what corresponds to the irradiation of the P-polarized laser beam and is obtainable therefrom, the resulting extraneous substance is decided as an extraneous substance existing on the surface under examination, and wherein when the signal level which corresponds to the irradiation of the P-polarized laser beam and is obtainable from the light receiving system is greater than what corresponds to the irradiation of the S-polarized laser beam and is obtainable therefrom, the resulting extraneous substance is decided as an extraneous substance existing on the back surface under examination.

12. An apparatus for detecting an extraneous substance on a glass plate as claimed in claim 1, wherein the extraneous substance is a flaw of the glass plate.

* * * * *